United States Patent [19]

Clayton et al.

[11] 3,981,866

[45] Sept. 21, 1976

[54] PENICILLIN MONOESTERS, THEIR PRODUCTION AND INTERMEDIATES THEREOF

[75] Inventors: John Peter Clayton; Harry Ferres, both of Horsham, England

[73] Assignee: Beecham Group Limited, Great Britain

[22] Filed: Sept. 21, 1973

[21] Appl. No.: 399,326

[30] Foreign Application Priority Data

Sept. 8, 1972 United Kingdom............... 41756/72

[52] U.S. Cl............................. 260/239.1; 424/271
[51] Int. Cl.[2]............... C07D 499/12; C07D 499/72
[58] Field of Search...................... 260/239.1, 243 C

[56] References Cited
UNITED STATES PATENTS

| | | | |
|---|---|---|---|
| 3,647,783 | 3/1972 | Oirie | 260/239.1 |
| 3,697,507 | 10/1972 | Frederiksen et al. | 260/239.1 |
| 3,847,913 | 11/1974 | Gudtfredsen | 260/243 C |
| 3,864,340 | 2/1975 | Ishimaru et al. | 260/243 C |
| 3,925,372 | 12/1975 | Chauvette | 260/243 C |

*Primary Examiner*—Nicholas S. Rizzo
*Assistant Examiner*—David E. Wheeler

[57] ABSTRACT

Mono-esters of $\alpha$-carboxypenicillins and their preparation are described including intermediates for the mono-esters. The mono-esters are esterified on the $\alpha$-carboxy group. They are well absorbed orally and de-esterified in vivo to give high serum concentrations of the parent $\alpha$-carboxypenicillins.

11 Claims, No Drawings

PENICILLIN MONOESTERS, THEIR PRODUCTION AND INTERMEDIATES THEREOF

This invention relates to mono-esters of α-carboxypenicillins wherein the α-carboxy group is esterified, and to a method for their preparation.

According to the present invention there is provided a compound of formula (I) or a pharmaceutically acceptable salt thereof:-

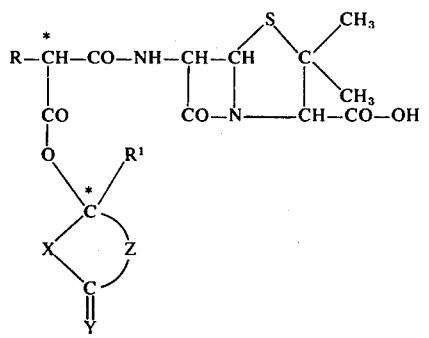

wherein R is an alkyl, cycloalkyl, aryl or heterocyclic group; X and Y are the same or different and each represents oxygen or sulphur; Z represents the residue of a lactone, thiolactone or dithiolactone ring system; $R^1$ represents hydrogen or an alkyl, alkenyl, alkynyl, aryl or aralkyl group or a functional substituent.

In formula (I) above, the carbon atoms marked * are asymmetric and the compounds can, therefore, exist as various optical isomers and mixtures of isomers. The present invention includes the pure optical isomers as well as mixtures of isomers. Preferably however, the α-carbon atom of the penicillin has the R (Rectus) absolute spatial configuration. (The configuration of the carbon atom of the lactone ring does not appear to be of any great importance.) In addition the configuration of the azetidinone ring of compounds (I) is preferably that shown in formula (IA), i.e. the configuration of the naturally occurring antibacterially active penicillins:-

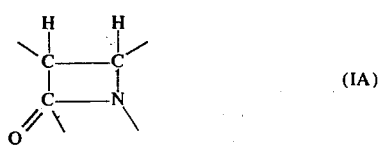

In formula (I), the group R is alkyl, cycloalkyl, aryl or heterocyclic group. Examples of specific groups R include methyl, ethyl, n- and iso- propyl, cyclopropyl, cyclopentyl, cyclohexyl, cycloheptyl, phenyl, 2- or 3- thienyl, tetrahydropyranyl, and thiacyclohexanyl. However, in the preferred compounds of this invention, R is a phenyl or 3- thienyl group.

Also in formula (I) above, Z represents the residue of a lactone, thiolactone or dithiolactone ring system. By way of example, Z may be a straight or branched chain saturated or unsaturated divalent hydrocarbon radical having from 2 to 12 carbon atoms and two or more carbon atoms in the radical may be joined in a carbocyclic or heterocyclic ring system. The radical Z may also carry one or more functional substituents such as hydroxy, alkoxy, halogen, nitro, amino or carboxyl groups. Specifically, in the preferred compounds of this invention, Z is a 1,2phenylene group which may carry one or more substituents such as alkoxy, nitro, or halogen substituents.

Preferably, in compounds of formula (I), both X and Y are oxygen.

The group $R^1$ in formula (I) is preferably hydrogen, but may also be, for example, lower alkyl, e.g. methyl or ethyl, lower alkenyl, e.g. vinyl or allyl, lower alkynyl e.g. ethynyl or propargyl; aryl, e.g. phenyl; or aralkyl, e.g. benzyl. $R^1$ may also be a functional group such as a hydroxy, alkoxy, halogen, amino or carboxyl group.

Pharmaceutically acceptable salts of compounds of formula (I) include non-toxic metallic salts such as sodium, potassium, calcium and aluminium, ammonium and substituted ammonium salts, e.g. salts of such non-toxic amines as trialkylamines, including triethylamine, procaine, dibenzylamine, N-benzyl-beta-phenethylamine, 1-ephenamine, $N,N^1$-dibenzylethylene-diamine, dehydroabietylamine, $N,N^1$-bis-dehydroabietylethylene-diamine, and other amines which have been used to form salts with benzylpenicillin.

In the presence of human and animal serum, the compounds of this invention are de-esterified, releasing the parent α-carboxypenicillin. They are well-absorbed when given by the oral route and give rise to high serum concentrations of the parent α-carboxypenicillin.

The compounds of this invention may be prepared by a process which comprises reacting 6-aminopenicillanic acid or a salt thereof or a silyl derivative of 6-aminopenicillanic acid with a reactive acylating derivative of a compound of formula (II):

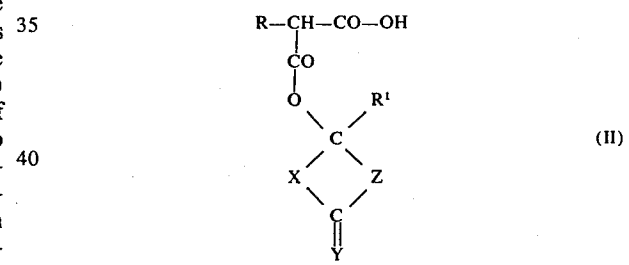

wherein R, $R^1$, X, Y and Z have the same meaning as in formula (I), and, if a silyl derivative of 6-aminopenicillanic acid was employed, thereafter removing the silyl groups from the resultant compound by hydrolysis or alcoholysis.

By the term "silyl derivative" of 6-aminopenicillanic acid we mean the product of the reaction between 6-aminopenicillanic acid and a silylating agent such as a halotrialkylsilane, a dihalodialkylsilane, a halotrialkoxysilane, a dihalodialkoxysilane, or a corresponding aryl or aralkyl silane, or a compound such as hexamethyldisilazane. In general halotrialkylsilanes are preferred, especially trimethylchlorosilane. The silylated derivatives of 6-aminopenicllanic acid are extremely sensitive to moisture and hydroxylic compounds, and after the reaction with acylating derivative of compounds (II), the silyl groups of the intermediate acylated compound can be removed by hydrolysis or alcoholysis.

A reactive acylating derivative of compound (II) is employed in the above reacton. Many suitable acylating derivatives are known from the literature of the synthesis of α-carboxybenzylpenicillin but examples of such derivatives include the acid chloride, anhydride or mixed anhydride.

The following Examples illustrate the present invention:

EXAMPLE 1

α-Phthalide ester of carbenicillin, sodium salt a. Phthalide hydrogen phenylmalonate Phenylmalonic acid (12.6 g; 0.07 M) and thionyl chloride (5.2 ml.; 0.07 M) were heated under reflux for 2 hrs. in anhydrous ether (50 ml.) containing 1-2 drops of dimethylformamide. At the end of this period the solvent and any remaining thionyl chloride were removed in vacuo. The oily residue was dissolved in anhydrous ether (75 ml.), o-phthalaldehydic acid (10.5g; 0.07 M) was added in one portion and the mixture heated under reflux for 2 hrs. The yellow reaction solution was cooled to ambient temperatures and extracted with saturated sodium bicarbonate solution (150 ml.) and the bicarbonate solution quickly washed with ether (100 ml.) and acidified to pH 1.0 with 5N hydrochloric acid (NB the bicarbonate layer should be made acidic as quickly as possible due to the lability of the phthalide ester group at alkaline pH values). A yellow oil precipitated out of the acidic solution and it was extracted into methylene dichloride (2×100 ml.) and the organic extracts were washed with water (2×100 ml.) and dried over anhydrous magnesium sulphate. Upon concentrating the dried methylene solution in vacuo to ca. ¼ volume the product crystallised as a white solid (6.0g.), m.p. 130°–131°. A second crop was obtained (4.6g.) m.p. 128°–130°, representing a total yield of 48.5%. i.r. (KBr) strong bands inter alia at: $1770 cm^{-1}$ $1700 cm^{-1}$ $1420 cm^{-1}$ $1275 cm^{-1}$ $1265 cm^{-1}$ $1215 cm^{-1}$ $1145 cm^{-1}$ $1050 cm^{-1}$ $960 cm^{-1}$ $750 cm^{-1}$ $695 cm^{-1}$ n.m.r. [$(CD_3)_2CO/D_2O$]: δ= 7.9–7.3 (1 OH. multiplet. phenyl and phthalide aromatics and

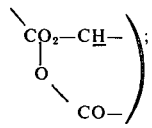

δ= 4.97(1H.s.

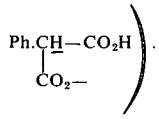

Upon standing a third peak developed at δ= 3.83 which is the methylene group in phthalide phenyl acetate formed by decarboxylation of phthalide hydrogen phenylmalonate.

$C_{17}H_{12}O_6$ requires: C, 65.38: H, 3.85; found: C, 64.83: H, 4.02 b. α-Phthalide α-carboxyphenylacetamidopenicillanate, sodium salt

Phthalide hydrogen phenylmalonate (6.2; 0.02 M) and thionyl chloride (1.5 ml.; 0.02M) were heated under reflux for 2 hrs. in dry methylene dichloride (100 ml.) containing 1-2 drops of dimethylformamide. As the reaction progressed the reagents slowly dissolved to give a clear yellow solution. The solvent and any unreacted thionyl chloride were removed in vacuo, anhydrous benzene (20 ml.) was added and evaporated in vacuo to ensure the removal of the final traces of thionyl chloride. The acid chloride of phthalide hydrogen phenylmalonate, which appeared as a viscous pale yellow oil, was dissolved in anhydrous acetone (100 ml.).

6-Aminopenicillanic acid (4.3 g; 0.02 M) in water (100 ml.) was treated with 1N sodium hydroxide (20 ml.), 1N sodium bicarbonate (30 ml.) and acetone (50 ml.) and then cooled to ca. 10°C. The half acid chloride solution was added in one portion and reaction mixture stirred at ambient temperatures for 2 hrs. The reaction mixture was washed with ether (3×100 ml.), covered with an ether layer (100 ml.) and acidified with dilute hydrochloride acid to pH 1.5. The ether layer was separated and the aqueous layer extracted with ether (2×100 ml.). The combined ether layers were washed with water (2×100 ml.) and dried over anhydrous magnesium sulphate. To the stirred ether solution a solution of sodium 2-ethylhexoate (S.E.H.) in methyl isobutylketone (ca. 2N solution) was added dropwise until no further precipitation of the product was evident. The white amorphous solid 4.6 g; 43.5%) was collected and washed well with anhydrous ether. Single spot on biochromatogram (solvent, butanol:ethanol:water) (against B, Subtilus) at $R_f$=0.67.

i.r (KBr) strong bands at $1770 cm^{-1}$ $1665 cm^{-1}$ $1600 cm^{-1}$ $1310 cm^{-1}$ $1210 cm^{-1}$ $1130 cm^{-1}$ $970 cm^{-1}$ $750 cm^{-1}$.

n.m.r. [$(CD_3)_2SO/D_2O$]: δ=7.80 (4H. m. phthalide aromatics); δ=7.57 (1H.s.

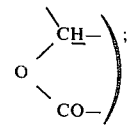

δ7.30
(5H. broad singlet. phenyl aromatics); δ=5.42 (3H m. β-lactams and α-proton); δ=4.05 (1H.s C-3 proton); δ=1.48 (6H.m. gem dimethyls). $NH_2OH$ assay = 186.6%

$C_{25}H_{21}N_2O_8S$ Na requires: C, 56.39; H, 3.95; N, 5.26; S, 6.02 found: C, 55.00; H, 4.23; N, 5.04; S. 5.91.

EXAMPLE 2

α-Phthalide ester of α-carboxy-3-thienylacetamidopenicillanic acid sodium salt.

a. Phthalide hydrogen 3-thienylmalonate

3-Thienylmalonic acid (13.0 g; 0.07 M) and thionyl chloride (5.2 ml. 0.07 M) were heated under reflux for 2 hr. in anhydrous ether (75 ml.) containing 1-2 drops of dimethylformamide. At the end of this period the solvent and any remaining thionyl chloride were removed in vacuo. The oily residue was dissolved in anhydrous 100 ml.), o-phthalaldehydic acid (10.5 g; 0.07 M) was added in one portion and the mixture heated under reflux for 2 hrs. The deep yellow reaction solution was cooled to ambient temps. and extracted with saturated sodium bicarbonate solution (200 ml.) and the bicarbonate solution quickly washed with ether (100 ml.) and acidified to pH 1.0 with 5N hydrochloric acid (NB the bicarbonate layer should be made acidic as quickly as possible due to the lability of the phthalide ester group at alkaline pH values.). An orange oil precipitated out of the acidic solution and it was extracted into methylene dichloride (2×100 ml.) and dried over anhydrous magnesium sulphate. Upon concentrating the dried methylene dichloride solution in vacuo to ca. ¼ volume the product crystallised on cooling to a yellow solid (8.2 g.), m.p. 127°–129°. On standing a second crop was obtained (5.0 g.), m.p. 126°–129°, representing a total yield of 59.4%.

i.r. (KBr) strong bands inter alia at: 1770 cm$^{-1}$ 1700 cm$^{-1}$ 1280 cm$^{-1}$ 1145 cm$^{-1}$ 1050 cm$^{-1}$ 960 cm$^{-1}$ 750 cm$^{-1}$ 720 cm$^{-1}$.

n.m.r. (CDCl$_3$): δ= 8.0–7.0 (8H. multiples. phthalide and thienyl aromatics and $$\overset{\diagdown}{CO_2} - \overset{CH-}{\underset{CO-}{\diagup O \diagdown}}$$

δ = 5.22

(1H. s.

and a small peak at δ=4.88 which is the methylene group in phthalide 3-thienylacetate formed by dicarboxylation of phthalide hydrogen 3-thienylmalonate. C$_{15}$H$_{10}$O$_6$S requires: C, 56.60; H, 3.14; S, 10.06; found: C, 56.64; H, 3.34; S, 9.95.

b. α-Phthalide α-carboxy-3-thienylacetamidopenicillanate, sodium salt.

Phthalide hydrogen 3-thienylmalonate (6.4 g; 0.02 M) and thionyl chloride (1.5 ml.; ca. 0.02 M) were heated under reflux for 2 hrs. in dry methylene dichloride (100 ml.) containing 1–2 drops of dimethylformamide. As the reaction progressed the reagents slowly dissolved to give a clear yellow solution. The solvent and any reacted chloride were removed in vacuo, anhydrous benzene (20 ml.) was added and evaporated in vacuo to ensure the removal of the final traces of thionyl chloride.

The acid chloride of phthalide hydrogen 3-thienylmalonate which appeared as a viscous pale yellow oil, was dissolved in anhydrous acetone (100 ml.).

6-Aminopenicillanic acid (4.3 g: 0.02M) in water (100 ml.) was treated with 1N sodium hydroxide (20 ml.), 1N sodium bicarbonate (30 ml.) and acetone (50 ml.) and then cooled to ca. 10°C. The half acid chloride solution was added in one portion and the reaction mixture stirred at ambient temperatures for 2 hrs. The reaction mixture was washed with ether (3×100 ml.), covered with an ether layer (100 ml.) and acidified with dilute hydrochloric acid to pH 1.5. The ether layer was separated and the aqueous layer extracted with ether (2×100 ml.). The combined ether layers were washed with water (2×100 ml.) and dried over anhydrous magnesium sulphate. A solution of sodium 2-ethylhexoate (S.E.H.) in methyl isobutyl ketone (ca 2N solution) was added dropwise to the stirred ether solution of the penicillin until no further precipitation of the product was evident. The pale yellow amorphous solid (2.9 g; 26.8%) was collected and washed well with anhydrous ether.

Single spot on biochromatogram (solvent, butanol:ethanol:water against B. Subtilis at R$_f$= 0.67.

i.r. (KBr) strong bands inter alia at 1770 cm$^{-1}$ 1670 cm$^{-1}$ 1600 cm$^{-1}$ 1310 cm$^{-1}$ 1130 cm$^{-1}$ 970 cm$^{-1}$ 750 cm$^{-1}$.

n.mr. [(CD$_3$)$_2$SO/D$_2$O]; δ=7.80 (4H. m. phthalide aromatics); δ= 7.60–7.05 (4H.m. thienyl aromatics and δ=5.40 (3H. m. β-lactams and α-proton); δ=4.08 (1H.s. c-3 proton); δ=1.45 (6H.m. gem dimethyls).
NH$_2$OH assay = 181.8%
C$_{23}$H$_{19}$N$_2$O$_8$S$_2$Na requires: C, 51.30; H, 3.53; N, 5.20; S, 11.90. found: C, 50.79; H, 3.79; N, 5.10; S, 11.92.

EXAMPLE 3 a. α-(5,6-Dimethoxyphthalide)-α-carboxyphenylacetamidopenicillanate, sodium salt Procedure followed was the same as that described in detail in example 1, i.e. 5,6-dimethoxyphthalidyl hydrogen phenylmalonate and thionyl chloride were reacted in methylene dichloride to give the acid chloride which was then used to acylate 6-aminopenicillanic acid. The product α-(5,6-dimethoxyphthalide)-α-carboxyphenylacetamidopenicillanate was isolated in the usual way as a white sodium salt in 28% yield.

n.m.r. [(CD$_3$)$_2$SO/D$_2$O]: δ= 1.49 (6H, m, gem dimethyls); 3.54 (1H. broad s. C-3 proton); 3.92 (6H. s. —O—CH$_3$); 5.32 (3H, m, gem dimethyls and PhCH—); 7.32 (8H. m. phenyl, phthalide aromatics and phthalide C-3 proton); 8.1–9.4 (1H. exchangeable in D$_2$O. —CONH).

$_{max}$(KBr): 1768, 1600, 1500, 1349, 1286, 1122, and 974 cm$^{-1}$.

Single spot on biochromatogram (butanol:ethanol:water system) against B subtilis at R$_f$= 0.54. Hydroxylamine assay = 180.5%.

b. α-(5,6-Dimethoxyphthalide)-α-carboxy-3-thienylacetamidopenicillanate, sodium salt Procedure followed was as described in example 2 except that 5,6-dimethoxyphthalidyl hydrogen 3-thienylmalonate was employed. The product was isolated in the usual way as a white amorphous sodium salt, in low yield.

We claim:

1. A process for the preparation of a compound of formula (I) or a pharmaceutically acceptable salt thereof:

(I)

wherein R is lower alkyl, cycloalkyl of 3–6 carbon atoms, phenyl or 2- or 3-thienyl, tetrahydropyranyl or thiacyclohexanyl; X and Y are the same or different and each represents oxygen or sulphur; Z is 1,2-phenylene unsubstituted or substituted by one or more of alkoxy, nitro and halogen; $R^1$ represents hydrogen, lower alkyl, lower alkenyl, lower alkynyl, phenyl, benzyl, hydroxy, alkoxy, halogen, amino or carboxyl, by reacting 6-aminopenicillanic acid or a pharmaceutically acceptable salt thereof or a silylated 6-aminopenicillanic acid with a reactive N-acylating derivative of a compound of formula (III):

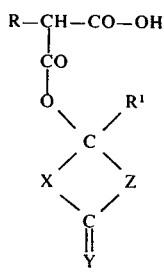

(III)

wherein R, $R^1$, X, Y and Z have the same meaning as in formula (I), and when a silylated 6-aminopenicillanic acid is employed, thereafter removing the silyl groups from the resultant compound by hydrolysis or alcoholysis.

2. A process as claimed in claim 1 wherein the reactive N-acylating derivative of compound (III) is an acid halide, anhydride or mixed anhydride.

3. A process as claimed in claim 1 wherein in compound (III) X and Y are each oxygen or sulphur, $R^1$ is hydrogen, R is phenyl or 3-thienyl, and Z is a 1,2-phenylene or 4,5-dimethoxy-1,2-phenylene group.

4. A compound of formula (I) or a pharmaceutically acceptable salt thereof:

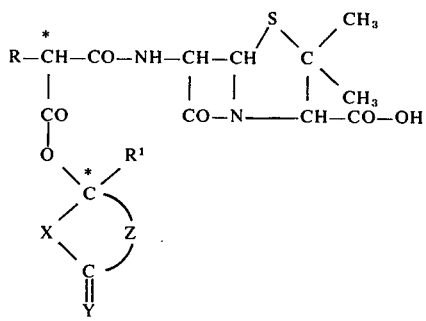

(I)

wherein R is lower alkyl, cycloalkyl of 3–6 carbon atoms, phenyl, or 2- or 3-thienyl, tetrahydropyranyl or thiacyclohexanyl; X and Y are the same or different and each represents oxygen or sulphur; Z is 1,2-phenylene unsubstituted or substituted by one or more of alkoxy, nitro and halogen; $R^1$ represents hydrogen, lower alkyl, lower alkenyl, lower alkynyl, phenyl, benzyl, hydroxy, alkoxy, halogen, amino or carboxyl.

5. A compound as claimed in claim 4 wherein R is a phenyl or 3-thienyl group.

6. A compound as claimed in claim 4 wherein X and Y are both oxygen or sulphur and $R^1$ is hydrogen.

7. A compound as claimed in claim 4, wherein Z is a 1,2-phenylene or 4,6-dimethoxy-1,2-phenylene group.

8. The α-phthalide ester of α-carboxyphenylacetamidopenicillanic acid of formula:

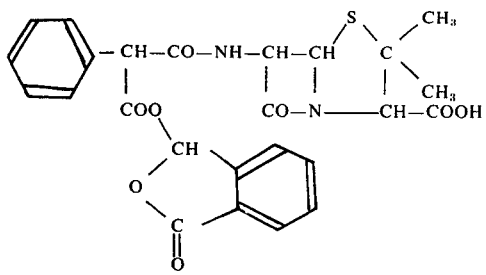

or a pharmaceutically acceptable salt thereof.

9. The α-phthalide ester of α-carboxy-3-thienylacetamidopenicillanic acid of formula:

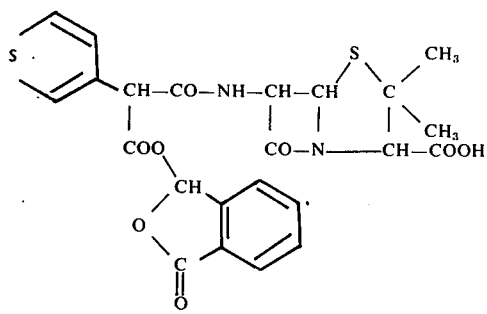

or a pharmaceutically acceptable salt thereof.

10. The α-3,5-dimethoxyphthalide ester of α-carboxyphenylacetamido penicillanic acid of formula:

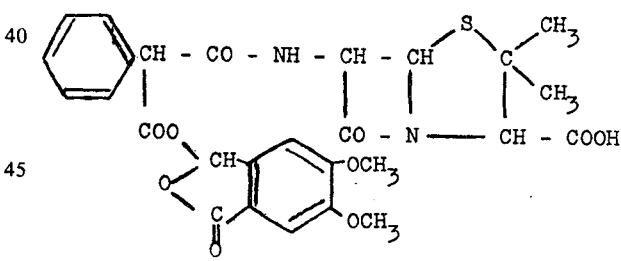

or a pharmaceutically acceptable salt thereof.

11. The α-3,5-dimethoxyphthalide ester of α-carboxy-3-thienylacetamido penicillanic acid of formula:

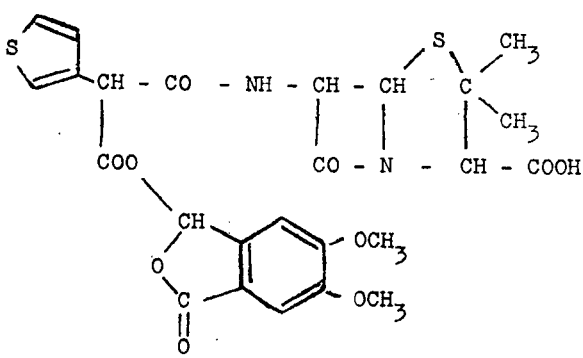

* * * * *